United States Patent
Chee et al.

(10) Patent No.: US 9,813,239 B2
(45) Date of Patent: Nov. 7, 2017

(54) SYSTEM AND METHOD FOR PROVIDING MASSAGE RELATED SERVICES

(71) Applicant: OSIM INTERNATIONAL LTD, Singapore (SG)

(72) Inventors: Evan Chee, Singapore (SG); Elwyn Kwang Ling Ng, Singapore (SG); Kia Tong Tan, Singapore (SG)

(73) Assignee: OSIM INTERNATIONAL LTD, Singapore (SG)

( * ) Notice: Subject to any disclaimer, the term of this patent is extended or adjusted under 35 U.S.C. 154(b) by 95 days.

(21) Appl. No.: 14/894,165

(22) PCT Filed: Jun. 3, 2013

(86) PCT No.: PCT/SG2013/000232
§ 371 (c)(1),
(2) Date: Nov. 25, 2015

(87) PCT Pub. No.: WO2014/196922
PCT Pub. Date: Dec. 11, 2014

(65) Prior Publication Data
US 2016/0127129 A1    May 5, 2016

(51) Int. Cl.
H04L 29/06  (2006.01)
H04L 9/08  (2006.01)
(Continued)

(52) U.S. Cl.
CPC ............ *H04L 9/0866* (2013.01); *G05B 15/02* (2013.01); *G06F 3/04817* (2013.01);
(Continued)

(58) Field of Classification Search
CPC .... A61H 2201/0149; A61H 2201/5012; A61H 23/00; A61H 7/00; G06F 19/3412;
(Continued)

(56) References Cited

U.S. PATENT DOCUMENTS 6,290,661 B1    9/2001    Cutler et al.
9,078,523 B2 *  7/2015    Menard ................... A47C 1/12
(Continued)

FOREIGN PATENT DOCUMENTS

CN    100556390    11/2009
CN    102263776    11/2011
(Continued)

OTHER PUBLICATIONS

Tricia Ong, "OSIM Uinfinity Massage Chair", Retrieved From http://vaingloriousyou.blogspot.sg/2013/09/osim-uinfinity-massage-chair.html, Published Sep. 23, 2013.*
(Continued)

*Primary Examiner* — Chau Le
(74) *Attorney, Agent, or Firm* — Baker & McKenzie LLP

(57) ABSTRACT

A method of providing massage related services comprises providing a massage apparatus, establishing a connection between a terminal device and a server computer, transferring a massage program executable on the massage apparatus from the server computer to the terminal device, establishing a connection between the terminal device and the massage apparatus, and transferring the massage program from the terminal device to the massage apparatus. Once the new massage program is downloaded in the massage apparatus, a graphical user interface displayed by a remote controller of the massage apparatus can be updated with a new icon associated with the new massage program. The new massage program then can be executed either from the remote controller or the terminal device. In some embodiments, a massage apparatus and a system including the massage apparatus are also described.

17 Claims, 10 Drawing Sheets

(51) Int. Cl.
  *G06F 19/00* (2011.01)
  *G05B 15/02* (2006.01)
  *G06F 3/0481* (2013.01)
  *A61H 7/00* (2006.01)
  *A61H 23/00* (2006.01)

(52) U.S. Cl.
  CPC ............ *G06F 19/3481* (2013.01); *A61H 7/00* (2013.01); *A61H 23/00* (2013.01); *A61H 2201/0149* (2013.01); *A61H 2201/5012* (2013.01); *G06F 19/3412* (2013.01); *H04L 2209/24* (2013.01)

(58) Field of Classification Search
  CPC ............. G06F 19/3481; G06F 3/04817; H04L 2209/24; H04L 9/0866
  See application file for complete search history.

(56) References Cited

U.S. PATENT DOCUMENTS

| | | | | |
|---|---|---|---|---|
| 2002/0111570 | A1* | 8/2002 | Cutler | A61H 23/0263 601/15 |
| 2004/0127822 | A1* | 7/2004 | Eisenberg | A45D 44/02 601/49 |
| 2005/0131273 | A1* | 6/2005 | Asano | A61M 21/00 600/27 |
| 2006/0129811 | A1* | 6/2006 | Fiske | H04L 9/0822 713/167 |
| 2006/0217641 | A1 | 9/2006 | Tanizawa et al. | |
| 2007/0171372 | A1* | 7/2007 | Seal | A61B 3/005 351/245 |
| 2008/0185888 | A1* | 8/2008 | Beall | G06Q 30/0273 297/217.4 |
| 2008/0188782 | A1* | 8/2008 | Carkner | A61H 9/0078 601/151 |
| 2009/0076844 | A1* | 3/2009 | Koegen | G06F 19/3418 705/2 |
| 2009/0253969 | A1* | 10/2009 | Wu | A61B 5/6887 600/301 |
| 2010/0030122 | A1* | 2/2010 | Gaspard | A61H 7/004 601/136 |
| 2010/0198120 | A1* | 8/2010 | Tago | A61H 1/0237 601/134 |
| 2011/0055720 | A1* | 3/2011 | Potter | G06F 3/017 715/747 |
| 2015/0169124 | A1* | 6/2015 | Le | A61H 15/0078 345/173 |

FOREIGN PATENT DOCUMENTS

| | | |
|---|---|---|
| CN | 202505740 | 10/2012 |
| CN | 202699870 U | 1/2013 |
| CN | 202711461 U | 1/2013 |
| JP | 2003-250850 A | 9/2003 |
| JP | 2005-058404 A | 3/2005 |
| JP | 2005-334136 A | 12/2005 |
| TW | M419998 U1 | 1/2012 |

OTHER PUBLICATIONS

ImPRESSions PR pte ltd, "OSIM Introduces the Only Massage Chair with an iPhone App of Its Own", myNewsdesk, Retrieved From http://www.mynewsdesk.com/sg/pressreleases/osim-introduces-the-only-massage-chair-with-an-iphone-app-of-its-own-782806, Published Aug. 6, 2012.*
Taiwan Office Action, Taiwan Application No. 103119099, dated Dec. 16, 2015, 14 pages.
International Search Report and Written Opinion, PCT/SG2013/000232, dated Aug. 5, 2013, 10 pages.
Japanese Office Action issued by the Japanese Patent Office dated Apr. 5, 2017 in connections with Japanese Patent Application No. 2016516482.
Office Action issued by PRC State Intellectual Property Office in corresponding Chinese application No. 201380077181.1, dated Feb. 3, 2017.

\* cited by examiner

SYSTEM AND METHOD FOR PROVIDING MASSAGE RELATED SERVICES

CROSS-REFERENCE TO RELATED APPLICATION(S)

This patent application is a national phase filing under section 371 of PCT/SG2013/000232, filed Jun. 3, 2013, which is incorporated herein by reference in its entirety.

BACKGROUND

1. Field of the Invention

The present invention relate to systems and methods for providing massage related services using a massage apparatus.

2. Description of the Related Art

Massage apparatuses currently available on the market include massage chairs equipped with a massage member capable of applying diverse types of massage actions on a user's body. According to the needs, a user may select a massage program corresponding to a predetermined combination of movement and pressure actions of the massage member for producing certain desirable relaxing effects. Unfortunately, the existing massage apparatuses usually include a fixed set of predetermined massage programs, which may not permit a flexible usage of the massage apparatus and limit the effectiveness of the massages.

Therefore, there is a need for massage apparatuses that can address at least the foregoing issues and provide enhanced massage experience.

SUMMARY

The present application describes systems and methods of providing massage related services that can enrich the user's experience in using a massage apparatus. In one embodiment, the massage apparatus includes a massage unit, a driver operable to drive motion of the massage unit, and a microcontroller connected with the driver, wherein the microcontroller is configured to connect with an external device, receive a program code of a massage program from the external device and store the massage program in a memory, and execute the massage program through the massage unit to apply a sequence of massage actions on a body.

In certain embodiments, the massage apparatus further includes a remote controller operable to show one or more icons associated with massage programs available in the massage apparatus. Once a new massage program is downloaded, a graphical interface displayed by the remote controller is also updated with a new graphical icon selectable by a user to execute the newly downloaded massage program.

In other embodiments, a method of dispensing massage related services is described. The method comprises providing a massage apparatus, establishing a connection between a terminal device and a server computer, transferring a massage program executable on the massage apparatus from the server computer to the terminal device, establishing a connection between the terminal device and the massage apparatus, and transferring the massage program from the terminal device to the massage apparatus.

DETAILED DESCRIPTION OF THE EMBODIMENTS

Figure 1:
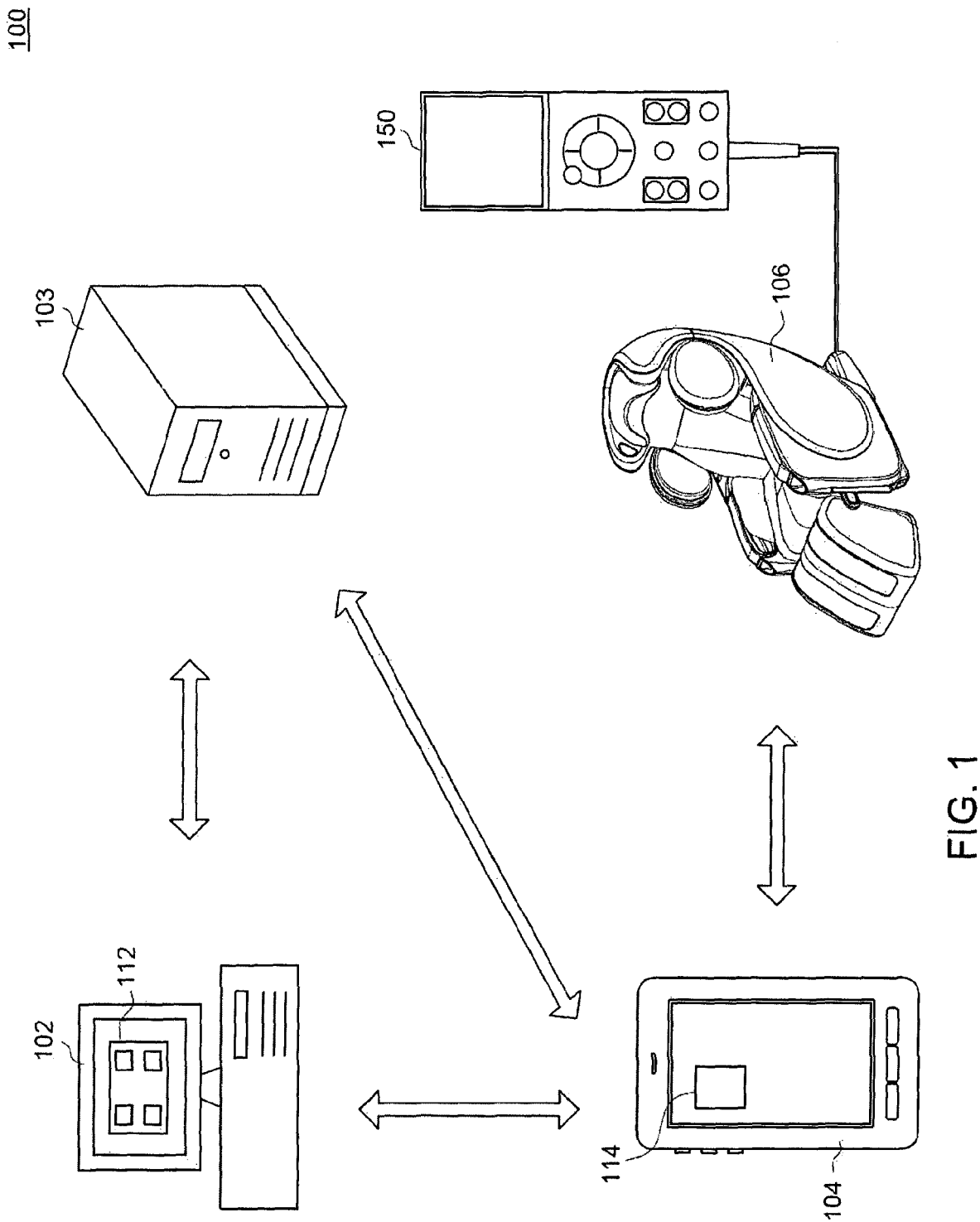
FIG. 1 is a schematic view illustrating an embodiment of a system of providing massage related services.

FIG. 1 is a schematic diagram illustrating an embodiment of a system of providing massage related services 100. The system 100 can include two server computers 102 and 103, a terminal device 104 and a massage apparatus 106. The server computer 102 can host a digital application distribution platform 112 that allows the terminal device 104 to browse and download diverse application programs, and conduct various transactions. Examples of the digital application distribution platform 112 hosted by the server computer 102 can include the Apple App Store for terminal devices running with the iOS operating system developed by Apple Inc., and the Google Play Store for terminal devices running with the Android operating system developed by Google Inc.

The server computer 103 can store a plurality of massage programs that are executable on the massage apparatus 106, and connect with the terminal device 104 to transfer one or more of the massage programs via the terminal device 104 to the massage apparatus 106. In one embodiment, the server computer 103 can be maintained and operated by a selling entity of the massage programs, whereas the server computer 102 may serve as a transaction platform. A massage program can be transferred from the server computer 103 to the terminal device 104 as a result of a purchase transaction conducted between the terminal device 104 and the server computer 102.

The terminal device 104 can include a smart phone, a tablet computer, a laptop computer, a personal computer, and the like. The terminal device 104 can execute an application program 114 that allows the terminal device 104 to interact with the server computers 102 and 103 and the massage apparatus 106 for providing massage related services. More specifically, the application program 114 executed on the terminal device 104 can connect with the server computers 102 and 103 to conduct various transactions including, for example, receiving notifications about the release of new massage programs, conducting a purchase transaction for acquiring a new massage program, and downloading the massage program from the server computer 103. The application program 114 can also connect with the massage apparatus 106 to conduct various tasks including, for example, displaying current settings of the massage apparatus 106, transferring a purchased massage program to the massage apparatus 106, and controlling certain functionality of the massage apparatus 106.

The massage apparatus 106 can include any type of devices capable of applying massage to a body. In one embodiment, the massage apparatus 106 can be a massage chair. In other embodiments, the massage apparatus 106 may also be a massage belt, a foot massage apparatus, and the like. The massage apparatus 106 may be operable to apply massage, play music, provide interactive content, and receive updates of new massage programs from an external device, such as the terminal device 104. In one embodiment, the massage apparatus 106 can be provided with a remote controller 150 to facilitate its operation. In particular, the remote controller 150 can have a display capable of showing a list of massage programs for a user's selection.

Figure 2:
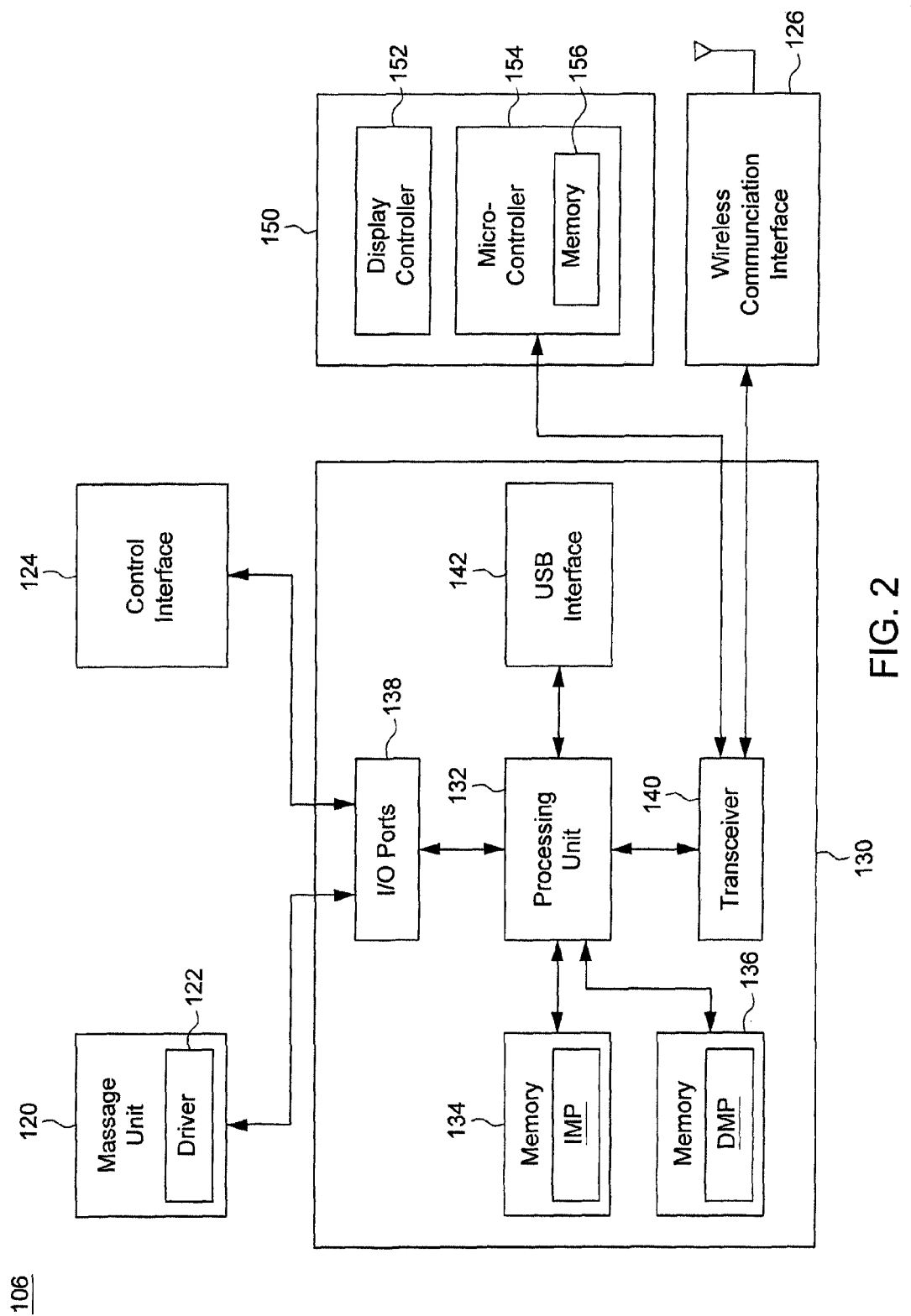
FIG. 2 is a simplified block diagram illustrating an embodiment of a massage apparatus.

FIG. 2 is a simplified block diagram illustrating one embodiment of the massage apparatus 106. The massage apparatus 106 can include a massage unit 120, a driver 122 associated with the massage unit 120, a control interface 124, a wireless communication interface 126, a microcontroller 130 and a remote controller 150. The massage unit 120 can include one or more mechanical components operable to apply various types of massage actions, such as kneading and/or tapping actions, scrapping actions and the like. Examples of components in the massage unit 120 can include a motor, an actuator, a pump, a solenoid, etc.

The driver 122 can be a circuit that provides the interface between the microcontroller 130 and the massage unit 120, and can be operable to drive operation of the component of the massage unit 120 according to control signals outputted by the microcontroller 130.

The control interface 124 can be connected with sensors and limit switches arranged in the massage apparatus 106, and can deliver various detection signals to the microcontroller 130 to provide information such as physical height of the user, limits of movements, motor revolutions, etc.

The wireless communication interface 126 can include a Bluetooth interface and/or Wi-Fi interface that enables data exchange between the microcontroller 130 of the massage apparatus 106 and other external devices in a wireless manner.

The microcontroller 130 can control and supervise the operation of the massage apparatus 106. In one embodiment, the microcontroller 130 can exemplary be a 32-bit Reduced Instruction Set Computing (RISC) microcontroller. The microcontroller 130 can select one of a plurality of massage programs stored internally, execute the massage program through the massage unit 120 to apply a sequence of massage actions on a user's body, and interact with the terminal device 104 via the wireless communication interface 126. In one embodiment, the microcontroller 130 can include a processing unit 132, a first and a second memory 134 and 136 for storing massage program codes, input/output (I/O) ports 138 through which the processing unit 132 can exchange signals with the driver 122 of the massage unit 120 and the control interface 124, a transceiver 140 for data exchange with the communication interface 130, and a Universal Serial Bus (USB) interface 142.

The memory 134 can store preset programming codes of massage programs IMP initially available in the massage apparatus 106. The separate memory 136 can store the programming codes of massage programs DMP that are loaded into the massage apparatus 106 by a user from an external device. In one embodiment, the memory 134 can exemplary be flash read-only memory (ROM), and the memory 136 can exemplary be electrically-erasable programmable read-only memory (EEPROM). The massage programs DMP may be downloaded from a server computer (e.g., the server computer 103) into the terminal device 104, and then transferred from the terminal device 104 to the massage apparatus 106 for storage in the memory 136. The massage programs DMP may be transferred from the external device to the massage apparatus 106 via the wireless communication interface 128 or the USB interface 142.

The transceiver 140 can be a Universal Asynchronous Receiver and Transmitter through which data can be received by the processing unit 132 of microcontroller 130 and transmitted to a component outside the microcontroller 130.

The remote controller 150 can be connected with the microcontroller 130. The remote controller 150 can include a display screen driven by a display controller 152, and a microcontroller 154 operable to receive user's inputs on the remote controller 150, to control graphical content shown on the display screen of the remote controller 150, and to interact with the microcontroller 130. In one embodiment, the microcontroller 154 of the remote controller 150 can include an internal memory 156 that stores graphical icons associated with the massage programs IMP and DMP. These graphical icons can be displayed on the screen of the remote controller 150 for facilitating the setting, control and operation of the massage apparatus 106 by the user.

Figure 3:
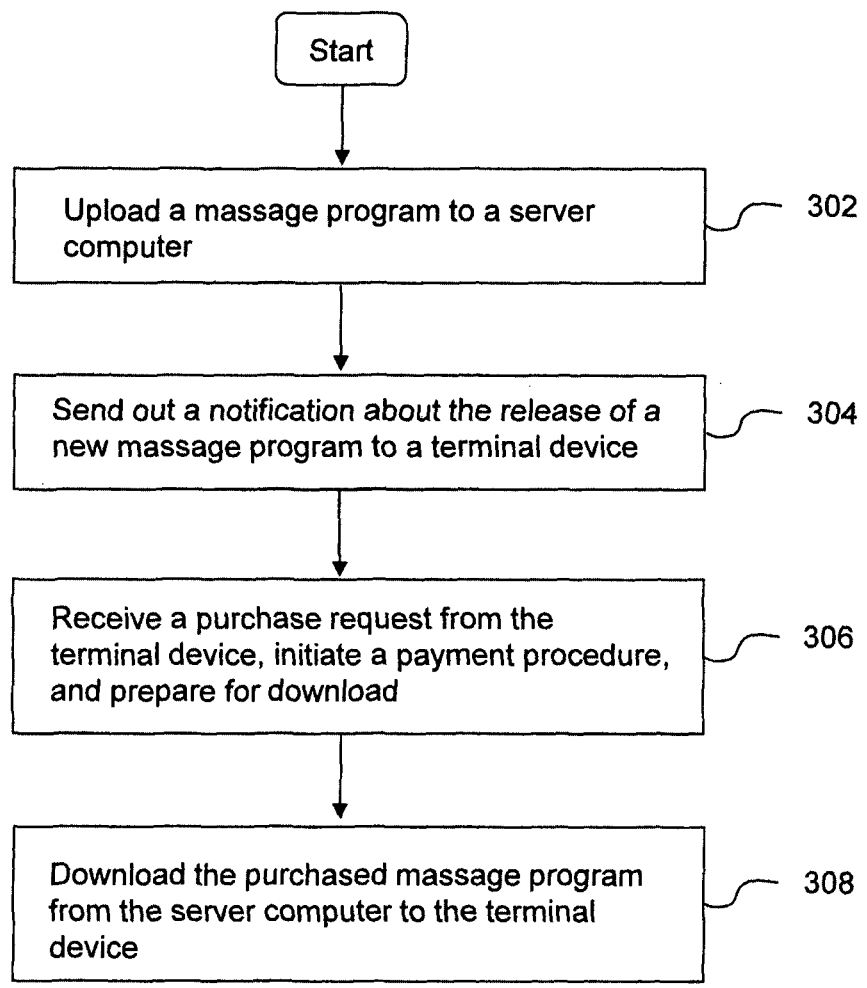
FIG. 3 is a flowchart illustrating method steps for providing massage programs at a server level.

In conjunction with FIGS. 1 and 2, FIG. 3 is a flowchart illustrating method steps for providing new massage programs at a server level. In initial step 302, a new massage program may be uploaded to the server computer 103. The new massage program may be uploaded in the form of one or more encrypted file to prevent corruption from a malicious agent. In addition to the massage program, the encrypted file(s) may also include graphical content defining graphical icons associated with the massage program.

In step 304, the server computer 103 may send out a notification about the release of the new massage program, which may be relayed via the server computer 102 to the terminal device 104. The terminal device 104 can be informed about the release of new massage programs via the application program 114.

In step 306, the server computer 102 can receive a purchase request from the terminal device 104, initiate a payment procedure, and send a request to the server computer 103 for downloading the purchased massage program.

In response to the download request from the server computer 102, the server computer 103 in step 308 can deliver one or more file of the purchased massage program to the terminal device 104. The purchased massage program may be downloaded from the server computer 103 to the terminal device 104 via Internet connection, for example.

Figure 4:
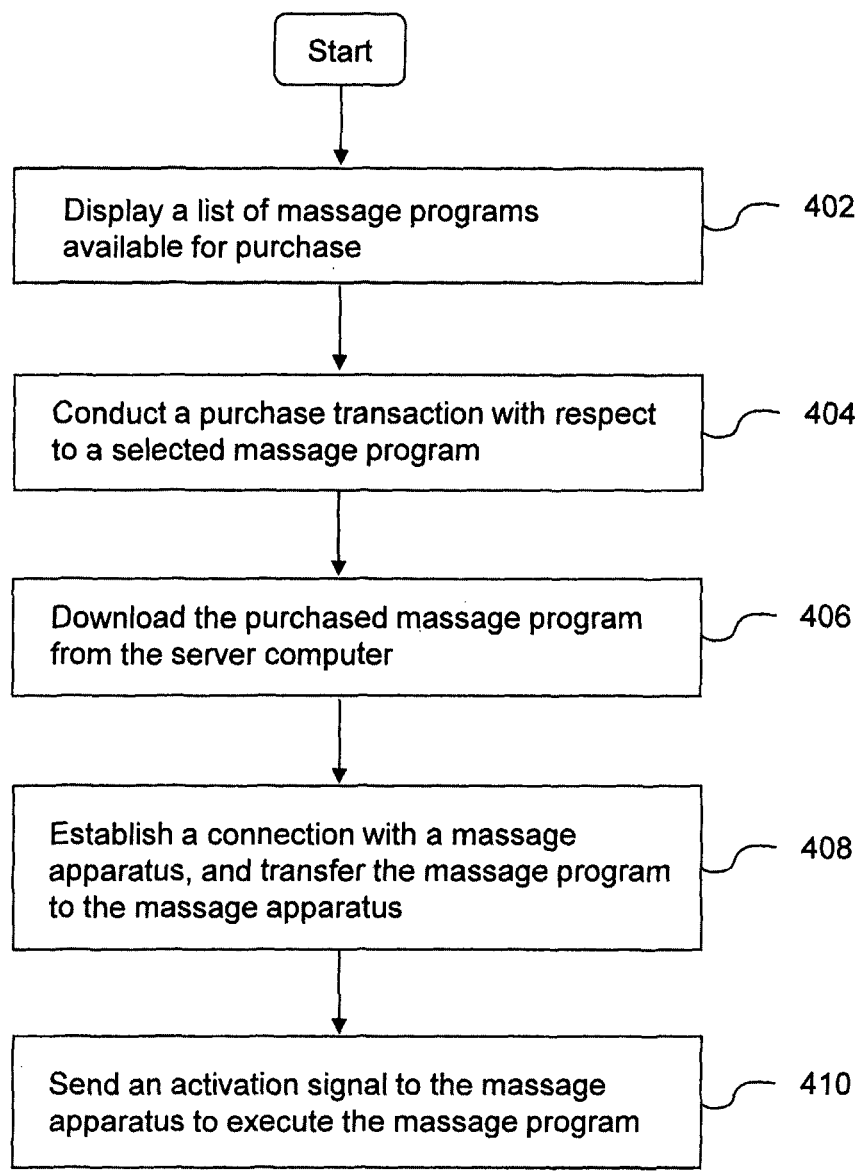
FIG. 4 is a flowchart illustrating method steps applied at a terminal device level for purchasing a massage program.
Figure 5B:
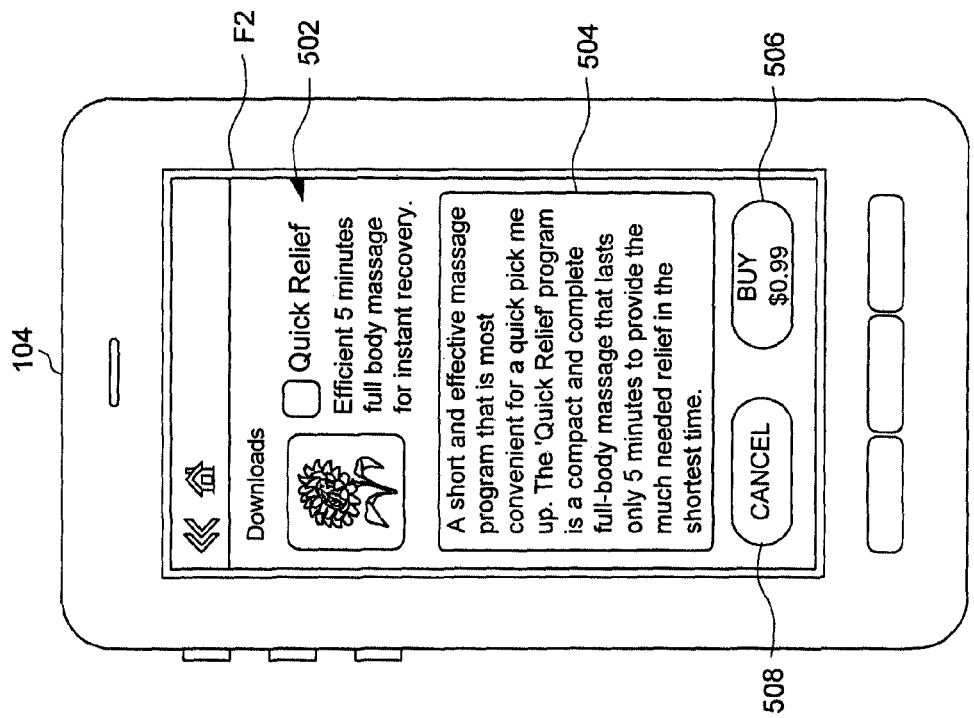
FIGS. 5A-5H are schematic views illustrating examples of displays on the terminal device occurring in an online transaction for buying a massage program.
Figure 5A:
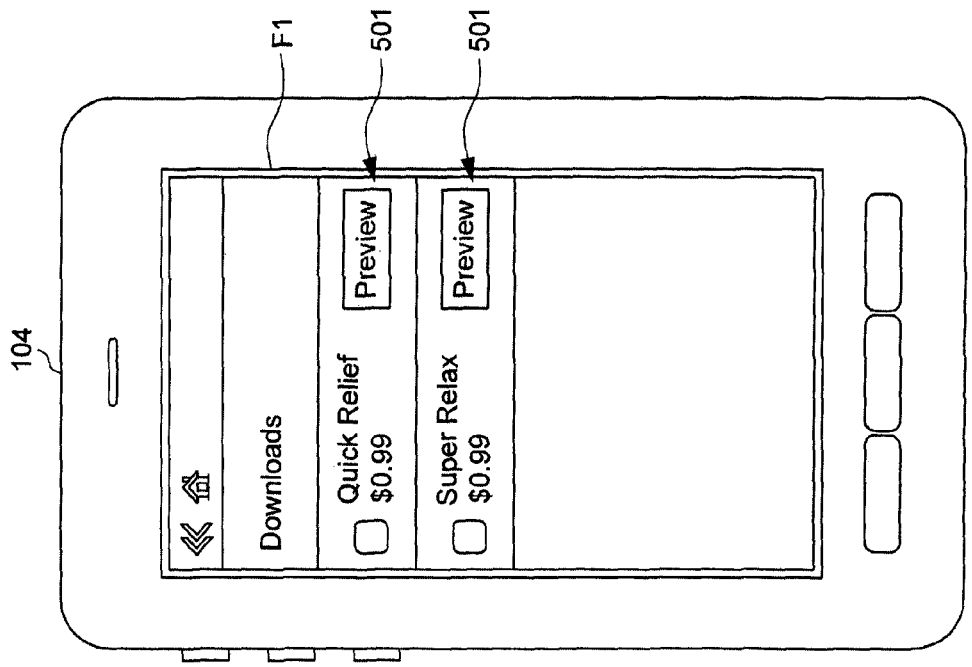

In conjunction with FIGS. 1 and 2, FIG. 4 is a flowchart illustrating method steps applied at the level of the terminal device 104 for purchasing online a new massage program, and FIGS. 5A-5H are schematic views illustrating examples of displays on the terminal device 104 occurring in the online purchase transaction. In step 402, the application program 114 running on the terminal device 104 can display an image frame F1 as shown in FIG. 5A listing a plurality of massage programs 501 available for purchase. The list of available massage programs 501 can be provided and updated by the server computer 102 or 103. When the user wants to preview one massage program of interest, the application program 114 can display an image frame F2 introducing the selected massage program. As better shown in FIG. 5B, the image frame F2 can include a field 502 identifying the name of the massage program, a portion 504 that describes the characteristics and features of the massage program, and a BUY icon 506 and a CANCEL icon 508 that can be selected by the user to respectively initiate or cancel the purchase transaction.

Figure 5D:
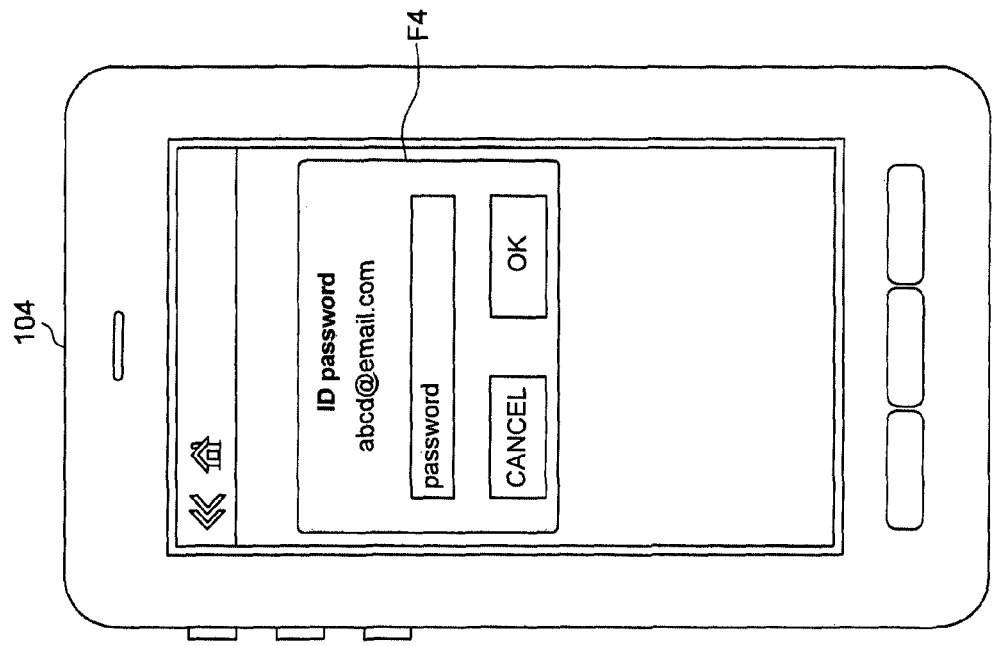
Figure 5C:
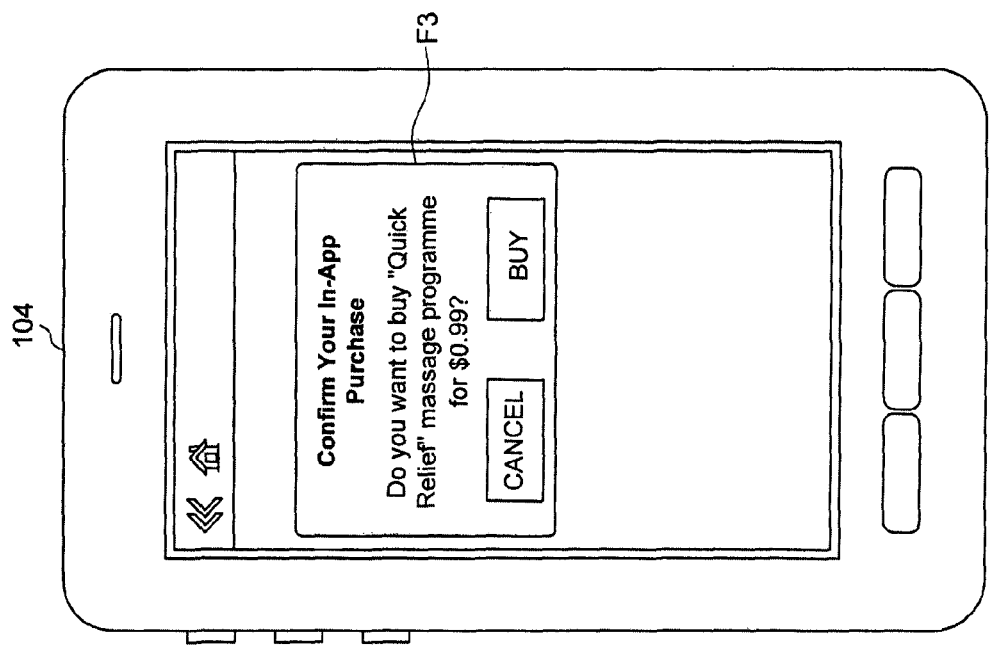
Figure 5F:
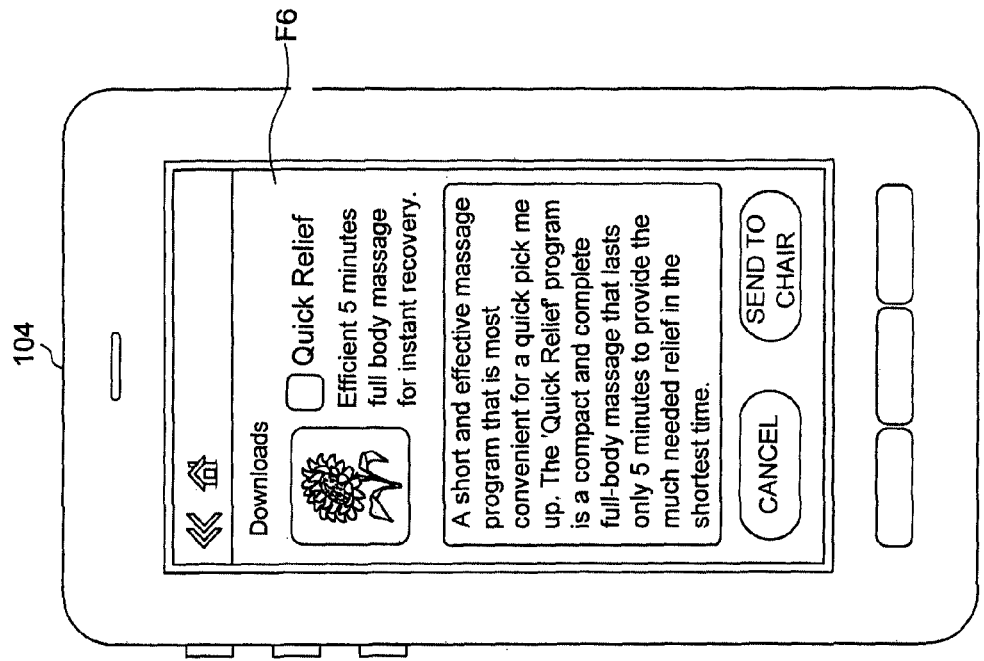

If the user wants to purchase the massage program, the application program 114 in step 404 can conduct a purchase transaction with respect to the selected massage program. For example, the application program 114 can display a confirmation window F3 as shown in FIG. 5C requesting the user to confirm the purchase of the selected massage program at the displayed price, and then query certain identification information via the query popup window F4 as shown in FIG. 5D.

Figure 5E:
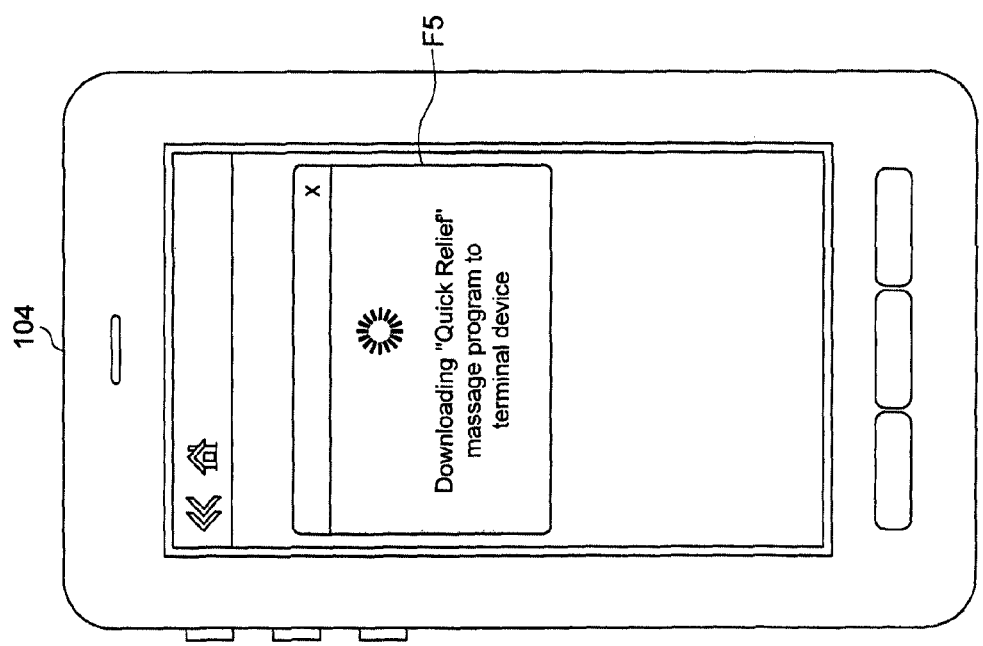

In next step 406, the application program 114 then can proceed to download the purchased massage program from the server computer 103. The download can be conducted, e.g., via internet connection. While the terminal device 104 is receiving one or more file of the purchased massage program, the application program 114 can display a download progress window F5 as shown in FIG. 5E. In one embodiment, the file(s) of the massage program may be downloaded to the terminal device 104 in an encrypted form that can be decrypted only on the massage apparatus 106. This may prevent corruption of the massage program during data transmission.

Once the download of the massage program to the terminal device 104 is completed, the application program 114 may display a query window F6 asking the user whether the downloaded massage program is to be transferred to the massage apparatus 106. Upon confirmation by the user, the application program 114 in step 408 can establish a connection with the massage apparatus 106 and proceed to transfer the downloaded massage program to the massage apparatus 106. This can be shown by the transfer progress window F7 illustrated in FIG. 5G.

Figure 5H:
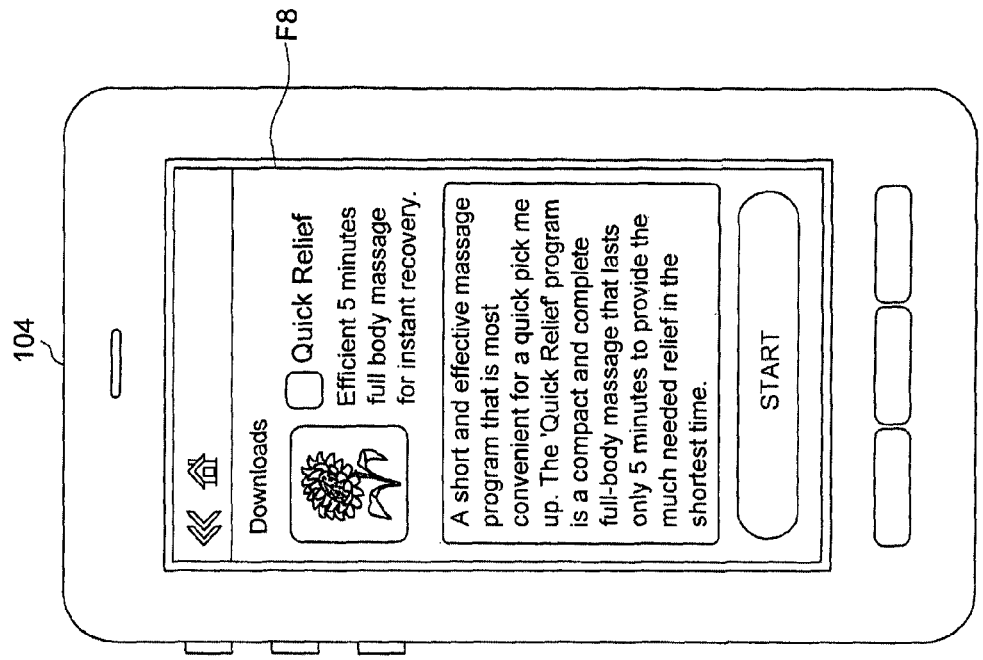
Figure 5G:
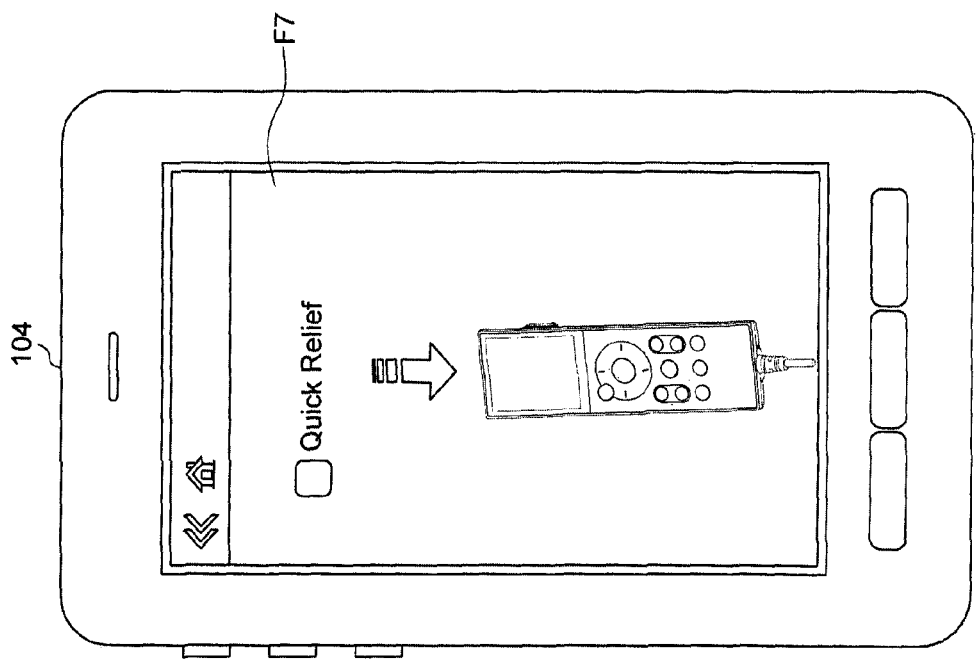

After the transfer of the massage program to the massage apparatus 106 is completed, the application program 114 can display a query window F8 as shown in FIG. 5H asking the user whether the massage apparatus 106 should start to run the massage program. In response to an activate request, the application program 114 in step 410 can send a signal to the massage apparatus 106 to trigger the execution of the massage program on the massage apparatus 106.

Figure 6:
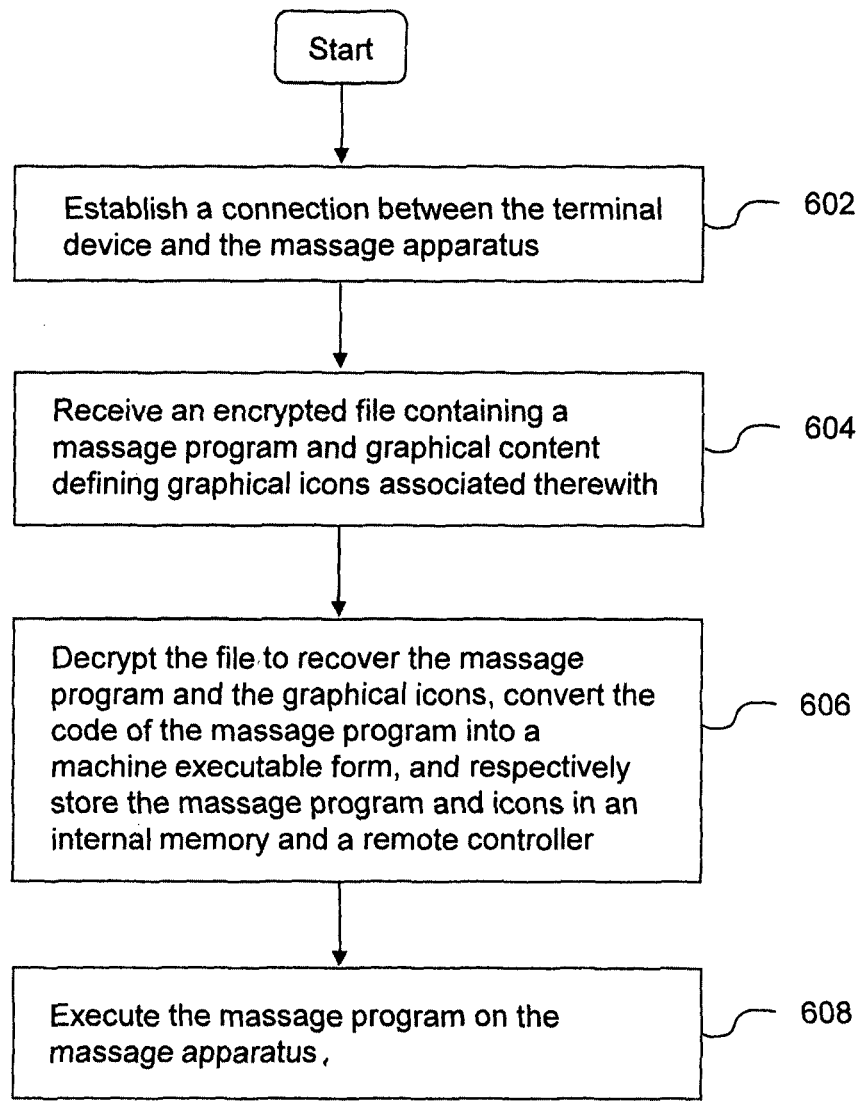
FIG. 6 is a flowchart illustrating method steps executed on the massage apparatus.

In conjunction with FIGS. 1 and 2, FIG. 6 is a flowchart illustrating method steps performed by the massage apparatus 106. In step 602, the microcontroller 130 in the massage apparatus 106 can turn on the wireless communication interface 128 in response to a request received from the terminal device 104 for establishing a connection between the terminal device 104 and the massage apparatus 106. The switch of the wireless communication interface 128 can be performed automatically by the system, or manually by using the remote controller 150.

In step 604, the massage apparatus. 106 can receive one or more encrypted file containing the program code of one massage program and graphical data of icons associated therewith. The transfer of the file(s) can be conducted via the wireless communication interface 128, e.g., through Bluetooth connection.

Figure 7B:
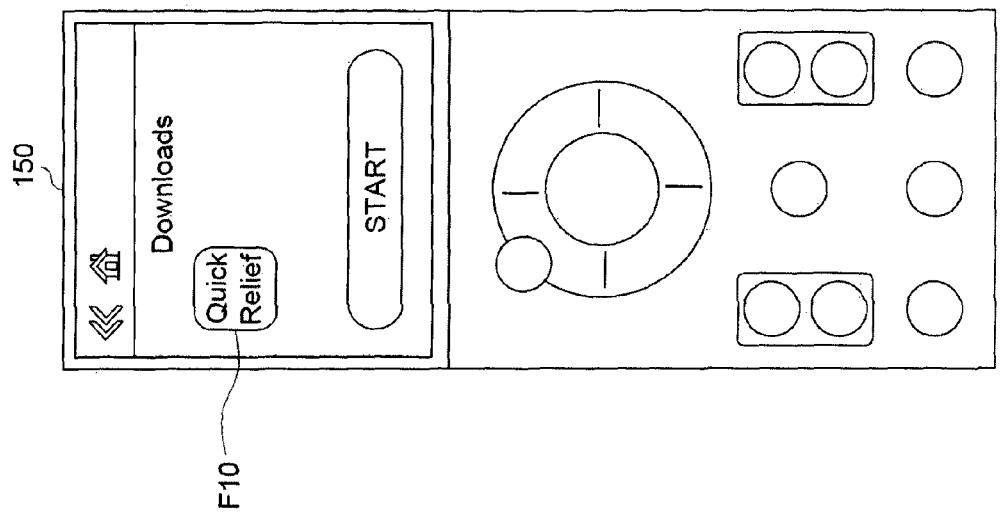
FIGS. 7A and 7B are schematic views illustrating examples of display on a remote controller of a massage apparatus with no downloaded programs and after downloading a new massage program.
Figure 7A:
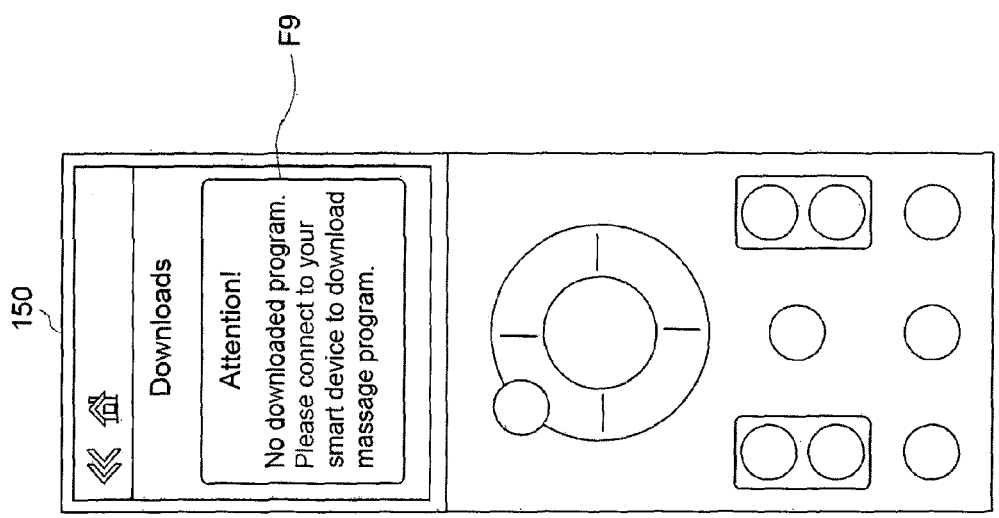

In step 606, the microcontroller 130 can decrypt the file(s) to recover the massage program code and the graphical icons (the icons may be defined as bitmap files), convert the code of the massage program into a machine executable form, and then respectively store the massage program code and the icons in the memory 136 and the remote controller 150. The graphical user interface at the remote controller 150 can be thereby updated to display the icon(s) associated with the downloaded massage program. FIGS. 7A and 7B are schematic views illustrating examples of display on the remote controller 150 with no downloaded programs and after the download of a new massage program. In FIG. 7A, the display of the remote controller 150 can exemplary show a window frame F9 indicating that there is no downloaded program in the massage apparatus 106. In FIG. 7B, the display of the remote controller 150 can show an icon F10 indicating that there is a newly downloaded program available for selection by the user.

In step 608, in response to an activation signal, the microcontroller 130 then can execute the new massage program through the massage unit 120 to apply a sequence of massage actions on the body of the user. The user can activate the massage apparatus 106 to execute the new massage program by, e.g., using the terminal device 104 or the remote controller 150.

While the foregoing describes the use of a wireless transmission between the terminal device 104 and the massage apparatus 106, it is worth noting that other methods can be applicable to transfer a new massage program to the massage apparatus 106. For example, the new massage program downloaded to the terminal device 104 first can be stored in an external device, e.g., another terminal device, a USB memory stick or any suitable storage devices. The external device then can be connected with the massage apparatus 106, and the new massage program can be transferred from the external device to the massage apparatus 106 via the USB interface 142. After the transfer is completed, steps 606 and 608 can be performed as described previously to install the new massage program in the massage apparatus 106.

At least one advantage of the systems and methods described herein includes the ability to download new massage programs, perform graphical user interface update on the remote controller of the massage apparatus, and using either the remote controller or the external device for execution of new downloaded massage programs on a massage apparatus. Accordingly, the massage apparatus can be used in in a more flexible manner, and the user can enjoy enriched massage experience on the massage apparatus.

Realizations of the systems and methods have been described only in the context of particular embodiments. These embodiments are meant to be illustrative and not limiting. Many variations, modifications, additions, and improvements are possible. Accordingly, plural instances may be provided for components described herein as a single instance. Structures and functionality presented as discrete components in the exemplary configurations may be implemented as a combined structure or component. These and other variations, modifications, additions, and improvements may fall within the scope of the inventions as defined in the claims that follow.

What is claimed is:
1. A massage apparatus comprising:
   a massage unit;
   a remote controller having a display screen;
   a driver operable to drive motion of the massage unit; and
   a microcontroller connected with the driver, wherein the microcontroller is configured to:
      connect with an external device;
      receive a program code of a massage program and graphical content of an icon associated with the massage program in an encrypted form from the external device to prevent corruption of the massage program during data transmission; and store the massage program in a memory;
      decrypt the massage program and the graphical content of the icon received from the external device;
      have the icon stored in the remote controller;
      display the icon on the display screen, the icon being selectable for executing the massage program; and execute the decrypted massage program through the massage unit to apply a sequence of massage actions on a body.

2. The massage apparatus according to claim 1, wherein the microcontroller includes an internal memory for storing the massage program received from the external device.

3. The massage apparatus according to claim 2, wherein the internal memory includes electrically-erasable programmable read-only memory.

4. The massage apparatus according to claim 1, further including a wireless communication interface through which the microcontroller receives the massage program from the external device.

5. The massage apparatus according to claim 4, wherein the wireless communication interface includes a Bluetooth interface, and/or a Wi-Fi interface.

6. The massage apparatus according to claim 1, further including a Universal Serial Bus interface through which the microcontroller receives the massage program from the external device.

7. The massage apparatus according to claim 1, wherein the microcontroller is further configured to:
store the icon in a second memory in the remote controller.

8. The massage apparatus according to claim 7, wherein the icon is defined in a bitmap file.

9. The massage apparatus according to claim 1, being configured as a massage chair.

10. A system of providing massage related services, comprising:
the massage apparatus according to claim 1;
a first and a second server computer; and
a terminal device operable to:
conduct a transaction with the first server computer to purchase the massage program;
download the massage program from the second server computer; and transfer the massage program to the massage apparatus.

11. The system according to claim 10, wherein the terminal device is operable to download the massage program from the second server computer via internet connection, and to transfer the downloaded massage program to the massage apparatus via a Bluetooth connection.

12. The system according to claim 10, wherein the massage program is downloaded to the terminal device in an encrypted form that is decryptable by the massage apparatus.

13. A method of providing massage related services, comprising:
providing a massage apparatus;
establishing a connection between a terminal device and a server computer;
transferring a massage program executable on the massage apparatus and graphical content of an icon associated with the massage program from the server computer to the terminal device;
establishing a connection between the terminal device and the massage apparatus; and
transferring the massage program and the graphical content of the icon contained in one or more encrypted files to prevent corruption of the massage program during data transmission from the terminal device to the massage apparatus;
through the massage apparatus, decrypting the one or more encrypted files to recover the massage program and the graphical content of the icon; and
displaying the icon on a display screen of a remote controller of the massage apparatus, the icon being selectable for executing the massage program.

14. The method according to claim 13, wherein the massage program is transferred from the server computer to the terminal device via internet connection.

15. The method according to claim 13, wherein the massage program is transferred from the terminal device to the massage apparatus via a wireless connection.

16. The method according to claim 15, wherein the wireless connection includes a Bluetooth connection.

17. The method according to claim 13, further including:
storing the decrypted graphical content of the icon associated with the massage program in a remote controller of the massage apparatus.

* * * * *